United States Patent
Phillips et al.

(10) Patent No.: US 10,201,670 B2
(45) Date of Patent: Feb. 12, 2019

(54) PRESSURE RELIEF ARRANGEMENT FOR OPEN SURGERY INSUFFLATION SYSTEM

(71) Applicants: FISHER & PAYKEL HEALTHCARE LIMITED, Auckland (NZ); Jonathan Stuart McFedries, Auckland (NZ); Colette Marie Hanley, Auckland (NZ)

(72) Inventors: Paul David Phillips, Auckland (NZ); Jonathan Stuart McFedries, Auckland (NZ); Colette Marie Hanley, Auckland (NZ)

(73) Assignee: FISHER & PAYKEL HEALTHCARE LIMITED, Auckland (NZ)

( * ) Notice: Subject to any disclaimer, the term of this patent is extended or adjusted under 35 U.S.C. 154(b) by 646 days.

(21) Appl. No.: 14/438,563

(22) PCT Filed: Oct. 25, 2013

(86) PCT No.: PCT/NZ2013/000192
§ 371 (c)(1),
(2) Date: Apr. 24, 2015

(87) PCT Pub. No.: WO2014/065678
PCT Pub. Date: May 1, 2014

(65) Prior Publication Data
US 2015/0290402 A1    Oct. 15, 2015

Related U.S. Application Data
(60) Provisional application No. 61/718,628, filed on Oct. 25, 2012.

(51) Int. Cl.
*A61M 13/00* (2006.01)
*A61M 16/16* (2006.01)
*A61M 16/10* (2006.01)

(52) U.S. Cl.
CPC .......... *A61M 13/003* (2013.01); *A61M 13/00* (2013.01); *A61M 13/006* (2014.02);
(Continued)

(58) Field of Classification Search
CPC .. A61M 13/00; A61M 13/003; A61M 13/006; A61M 2230/005
See application file for complete search history.

(56) References Cited

U.S. PATENT DOCUMENTS

| | | | |
|---|---|---|---|
| 5,006,109 A * | 4/1991 | Douglas | A61M 13/003 600/560 |
| 2006/0206051 A1* | 9/2006 | Hamilton | A61B 46/23 604/24 |

(Continued)

FOREIGN PATENT DOCUMENTS

| | | |
|---|---|---|
| CA | 2538456 C | 4/2005 |
| EP | 0856326 A1 | 8/1998 |

(Continued)

OTHER PUBLICATIONS

International Search Report; PCT/NZ2013/000192; dated Jan. 24, 2014; 3 pages.

*Primary Examiner* — Nathan R Price
*Assistant Examiner* — Anh Bui
(74) *Attorney, Agent, or Firm* — Knobbe, Martens, Olson & Bear, LLP

(57) ABSTRACT

A surgical humidification system includes a source of gas flow and a humidifier that receives the gas flow and outputs a humidified gas to a delivery conduit. The delivery conduit has an outlet and a suitable interface, such as a diffuser, is connected to the outlet. The interface can be positioned near or within an open surgical cavity of a patient to supply the humidified gas to the cavity. The system also includes a pressure relief arrangement that operates to relieve pressure from the system above a normal operating pressure. The
(Continued)

pressure relief arrangement can be located in a non-sterile portion of the system, such as upstream from the humidifier, for example.

38 Claims, 5 Drawing Sheets

(52) U.S. Cl.
CPC ........ *A61M 16/1095* (2014.02); *A61M 16/16* (2013.01); *A61M 16/107* (2014.02); *A61M 2205/3331* (2013.01); *A61M 2205/36* (2013.01); *A61M 2205/362* (2013.01); *A61M 2206/11* (2013.01); *A61M 2230/005* (2013.01)

(56) References Cited

U.S. PATENT DOCUMENTS

2007/0244424 A1   10/2007   Hameed et al.
2008/0178880 A1*   7/2008   Christopher ...... A61M 16/0051
                                                              128/204.23

FOREIGN PATENT DOCUMENTS

WO      WO 2004/096315 A2     11/2004
WO      WO 2006/094062 A1      9/2006

* cited by examiner

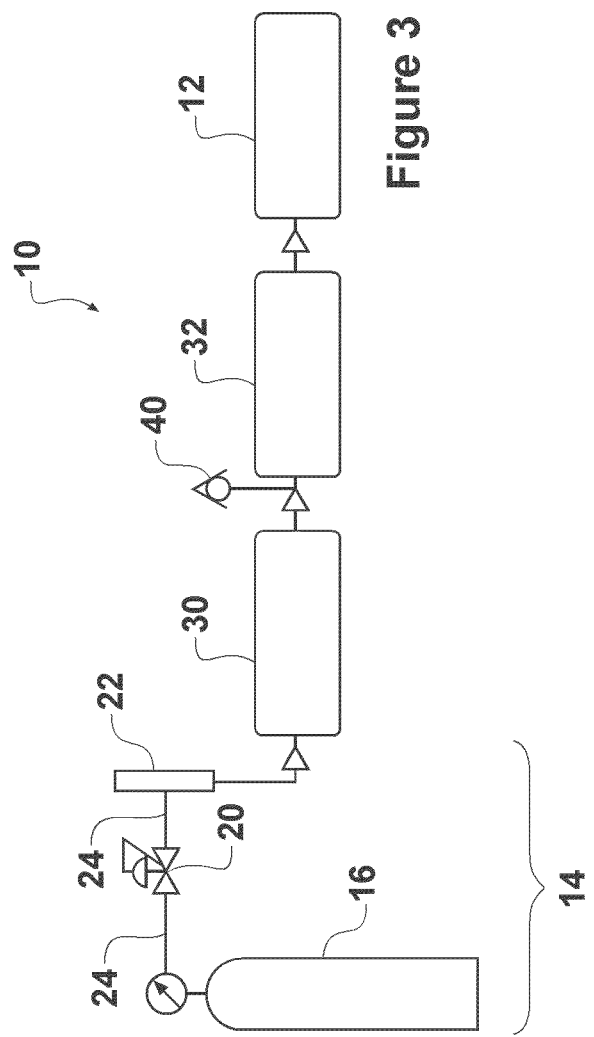

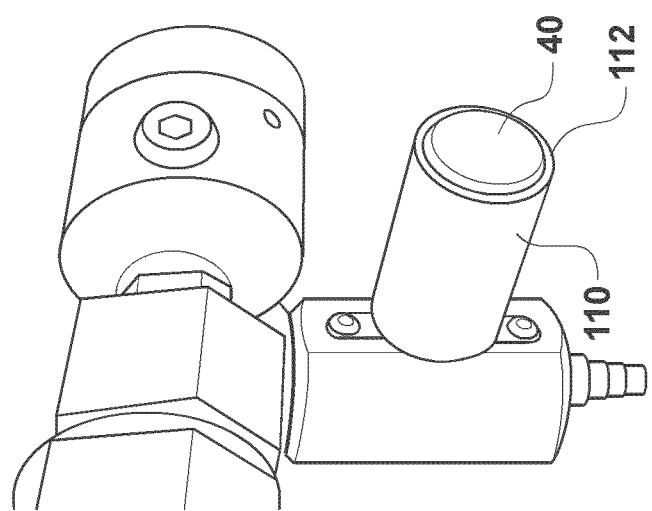

PRESSURE RELIEF ARRANGEMENT FOR OPEN SURGERY INSUFFLATION SYSTEM

BACKGROUND

Field

This disclosure relates generally to open surgery insufflation systems, and more particularly to humidified insufflation systems for open surgery.

Description of Related Art

Insufflation gases can be used in surgery for a variety of purposes. In open surgery, gas can be insufflated into a body cavity for de-airing, as in cardiac or thoracic surgery, for example. The insufflation gas can be inert or non-toxic, such as air or carbon dioxide ($CO_2$). Other insufflation gases that have been proposed are nitrogen gas ($N_2$), nitrogen dioxide $N_2O$, Argon (Ar) and Helium (He). Medical grade $CO_2$ can be supplied in cylinders and delivered to a patient at room temperature (e.g., between about 19 and 21 degrees Celsius), with a relative humidity approaching 0%. This gas is colder and drier than the environment inside the patient (e.g., about 37 degrees Celsius and a relative humidity of about 100%, respectively). Temperature and humidity of an insufflation gas can be adjusted to more closely approximate the environment inside the patient prior to delivery. Heating and humidifying the insufflation gas can decrease cellular damage or desiccation, limit adhesion formation, or reduce other deleterious effects. Although open surgery humidified insufflation systems exist, there remains room for improvement to, for example, increase the performance or reliability of the system.

SUMMARY

The systems, methods and devices described herein have innovative aspects, no single one of which is indispensable or solely responsible for their desirable attributes. Without limiting the scope of the claims, some of the advantageous features will now be summarized.

An aspect involves an open surgical insufflation system. The system comprises a gas source for providing a constant flow of insufflation gas. A humidifier receives the flow of insufflation gas from the gas source and warms and humidifies the flow of insufflation gas. A gas diffuser dispenses the warmed and humidified flow of insufflation gas from the humidifier into an open surgical cavity in direct contact with an external atmosphere to create an insufflation gas environment in the open surgical cavity. A pressure relief arrangement is activated in response to a system pressure above a threshold pressure and operates to reduce the system pressure when activated.

In some configurations, the pressure relief arrangement is located between the gas source and the humidifier.

In some configurations, the pressure relief arrangement is located upstream from the humidifier relative to a direction of the flow of insufflation gas within the system.

In some configurations, the pressure relief arrangement is located downstream from the humidifier relative to a direction of the flow of insufflation gas within the system.

In some configurations, the threshold pressure is no greater than about 12 psi.

In some configurations, the threshold pressure is no greater than about 9.5 psi.

In some configurations, the threshold pressure is no greater than about 5 psi.

In some configurations, the threshold pressure is between about 2 psi and about 9.5 psi.

In some configurations, the threshold pressure is between about 3 psi and about 5 psi.

In some configurations, the gas source comprises a gas bottle, a pressure regulator and a flow meter. In some configurations, the flow meter is adjustable and permits a flow rate of the flow of insufflation gas to be adjusted to between about 5 L/min and about 15 L/min. In some configurations, the flow rate can be adjusted to about 10 L/min.

In some configurations, the gas diffuser is constructed from a foam or foam-like material.

In some configurations the pressure relief arrangement may comprise a pressure relief valve.

In some configurations the pressure relief arrangement may comprise a protective shroud or cover around the pressure relief valve.

An aspect involves a method of providing insufflation gas therapy in an open surgical procedure. The method comprises providing a flow of an insufflation gas from a gas source. The flow of insufflation gas is passed through a humidification chamber to warm and humidify the flow of insufflation gas. The gas is diffused from a gas diffuser to within a surgical cavity that is open to the atmosphere to create an insufflation gas environment within the surgical cavity. Pressure within a system comprising the gas source, humidification chamber and the gas diffuser is relieved through a pressure relief valve that is separate from the gas diffuser in response to an increase in pressure within the system above a threshold pressure.

In some configurations, the pressure relief valve is located between the gas source and the humidification chamber.

In some configurations, the pressure relief valve is located upstream from the humidification chamber relative to a direction of the flow of insufflation gas within the system.

In some configurations, the pressure relief valve is located downstream from the humidification chamber relative to a direction of the flow of insufflation gas within the system.

In some configurations, the threshold pressure is no greater than about 12 psi.

In some configurations, the threshold pressure is no greater than about 9.5 psi.

In some configurations, the threshold pressure is no greater than about 5 psi.

In some configurations, the threshold pressure is between about 2 psi and about 9.5 psi.

In some configurations, the threshold pressure is between about 3 psi and about 5 psi.

In some configurations, the gas source comprises a gas bottle, a pressure regulator and a flow meter. In some configurations, the flow meter is adjusted so that a flow rate of the flow of insufflation gas is between about 5 L/min and about 15 L/min. In some configurations, the flow meter is adjusted so that the flow rate is about 10 L/min.

In some configurations, the gas diffuser is constructed from a foam or foam-like material.

An aspect involves a method of assembling an open surgical insufflation system. The method comprises connecting a gas source to a humidifier, the gas source configured to supply a constant flow of an insufflation gas and the humidifier configured to receive the flow of insufflation gas and warm and humidify the insufflation gas. A gas diffuser is connected to the humidifier, the gas diffuser configured to dispense the flow of insufflation gas to an open surgical cavity of a patient. A pressure relief valve is connected to the system, the pressure relief valve configured to reduce pressure within the system when the pressure reaches a threshold pressure.

In some configurations, the connecting of the pressure relief valve comprises connecting the pressure relief valve between the gas source and the humidifier.

In some configurations, the connecting of the pressure relief valve comprises connecting pressure relief valve at a location upstream from the humidifier relative to a direction of the flow of insufflation gas within the system.

In some configurations, the connecting of the pressure relief valve comprises connecting pressure relief valve at a location downstream from the humidifier relative to a direction of the flow of insufflation gas within the system.

In some configurations, the threshold pressure is no greater than about 12 psi.

In some configurations, the threshold pressure is no greater than about 9.5 psi.

In some configurations, the threshold pressure is no greater than about 5 psi.

In some configurations, the threshold pressure is between about 2 psi and about 9.5 psi.

In some configurations, the threshold pressure is between about 3 psi and about 5 psi.

In some configurations, the gas source comprises a gas bottle, a pressure regulator and a flow meter and the method comprises connecting the humidifier to the flow meter.

BRIEF DESCRIPTION OF THE DRAWINGS

Throughout the drawings, reference numbers can be reused to indicate general correspondence between reference elements. The drawings are provided to illustrate example embodiments described herein and are not intended to limit the scope of the disclosure.

FIG. 3 illustrates a modification of the system of FIG. 1, with the pressure relief valve positioned downstream from the humidifier.

FIGS. 4a and 4b illustrate a modification of the system of FIG. 1, with the pressure relief valve provided with a protective shroud.

DETAILED DESCRIPTION OF THE PREFERRED EMBODIMENTS

Figure 1:
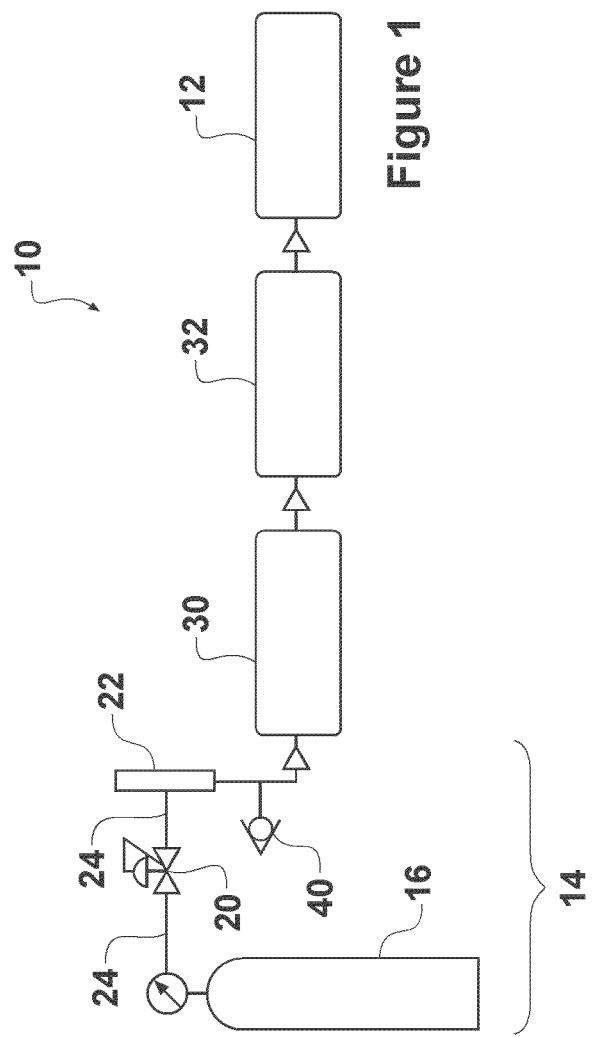
FIG. 1 illustrates an example open surgery insufflation system for delivering temperature-controlled and humidity-controlled insufflation gas to an open surgical site of a patient. The system includes a pressure relief valve positioned upstream from a humidifier of the system.

Described herein are methods and systems that relieve system pressure or limit the maximum pressure in an open loop or open insufflation system for use in open or direct access surgical procedures. It will be understood that although much of the description herein is in the context of open surgery, one or more features of the present disclosure can also be implemented in other scenarios where it is desirable to limit the output pressure of a gas, such as respiratory applications.

Insufflation gases can be used in a variety of surgical procedures. In open surgery, insufflation gases can be used in a body cavity for de-airing, which can decrease the risk of air embolism or, possibly, decrease the risk of infection of the surgical wound. In open surgical applications, the insufflation system is an open loop system that provides a generally constant flow of insufflation gas as a desired flow rate over a desirable period of time, which can encompass a portion or the entirety of the surgical procedure. Such an open loop system is in contrast to the (essentially) closed loop or feedback insufflation systems used in minimally invasive surgery, in which insufflation gas is provided discontinuously or on demand to maintain a relatively low pressure (e.g., 0.3 psi, 2 kPa) within the essentially sealed body cavity.

It has been discovered by the present inventor that, although insufflation systems for use in open surgery are open loop gas delivery systems, which deliver insufflation gas to the atmosphere, occlusion of the system can occur during normal or routine operation. Occlusion of the system can cause a rise in system pressure and, possibly, failure of or damage to components of the system. This failure or damage can cause a temporary or, in some cases, a complete interruption in the insufflation therapy. Thus, the present inventor has discovered that it can be desirable to provide for pressure relief in an open loop insufflation system.

In some configurations, the open loop surgery insufflation system incorporates a humidifier to warm and humidify the delivered insufflation gas. Body cavity environments can include cells that are susceptible to damage when exposed to relatively dry and cold gases. Insufflation gases can be relatively cold and dry and may cause damage to cells, damage that can be reduced or avoided through humidifying and warming the insufflation gas. Warming and humidifying the insufflation gas can reduce or prevent cellular desiccation. This can have a positive effect on post-operative pain that not only increases quality of care but reduces recovery time and increase department throughput. Warming and humidifying insufflation gases may reduce intra-operative hypothermia, reduce post-operative pain, and improve post-operative recovery.

Some embodiments described herein provide for a humidification system that is configured to deliver warm, humidified gas to a patient undergoing a surgical procedure. The gas is passed through a water chamber which is filled with water that is heated using a heater plate. Water evaporates in the chamber and combines with the gas which flows over it, thereby heating and/or humidifying the gas. The temperature of the gas can be maintained as it travels along a heated tube to an outlet port for delivery to the patient. The humidification system can monitor the temperature and flow rate of the gas at a chamber outlet, and control an amount of electrical power delivered to the heater plate to provide a gas having a desired temperature and humidity. Thus, surgical gas from a gas source (e.g., a gas bottle, wall source or the like) can be humidified and heated and delivered to the patient, enabling the targeted area to remain moist and warm.

Some embodiments described herein provide for a surgical humidification system that includes a humidifier control system configured to determine a mode of operation, a mode of control, a heater plate set point, or any combination of these. The humidifier control system can base this determination at least in part on feedback from components of the humidification system. The components of the humidification system can provide feedback through sensors or other electrical components, and feedback can include, for example, outlet gas temperature, heater plate temperature, heater plate power, gas flow rate, user input through user interface elements, duration of operation, and the like. Some embodiments of the humidifier control system can improve efficiency of the humidification system, provide an output gas with relatively consistent humidity and temperature, and provide greater control over temperature and humidity of the gas compared to control systems that do not incorporate system component feedback. The humidifier control system can provide at least some of these improvements through modules configured to process system component feedback and adjust output settings according to a control loop feedback mechanism. If provided, the humidifier can be controlled in any suitable manner, such as using a portion or an entirety of the control systems and methods disclosed in U.S. Provisional Patent Application No. 61/699,773, filed Sep. 11, 2012 and entitled SURGICAL HUMIDIFIER CONTROL.

FIG. 1 illustrates an example open surgery insufflation system 10 for delivering an insufflation gas to a patient 12 and, in particular, to an open surgical site of the patient 12, which can be, for example and without limitation, an area, cavity or wound (collectively referred to as a "cavity"). The open surgery insufflation system 10 comprises a gas source 14 for supplying a flow of insufflation gas. The insufflation gas can be any suitable gas for the desired purpose; however, in some configurations the insufflation gas is carbon dioxide ($CO_2$). As described above, $CO_2$ is often used as a surgical insufflation gas and is well-suited for open surgery insufflation because $CO_2$ is heavier than air and tends to displace air in an open surgical cavity.

The gas source 14 can be of any suitable arrangement to deliver a suitable flow of insufflation gas, which in some configurations is a constant flow of insufflation gas. In some configurations, the gas source 14 comprises a gas bottle 16 filled with a compressed insufflation gas, such as $CO_2$. However, in other configurations, the insufflation gas could be supplied by another gas supply, such as a wall supply (i.e., gas supplied via appropriate conduit from a remote reservoir) for example and without limitation. The gas source 14 can also comprise a pressure regulator 20 if necessary or desirable to regulate the pressure of the flow of insufflation gas provided by the gas bottle 16 or other gas supply. In some configurations, the gas bottle 16 contains insufflation gas (e.g., $CO_2$) that is pressurized to a relatively high pressure (e.g., about 5,000 kPa or about 725 psi). The pressure regulator 20 can reduce the pressure of gas supplied by the gas bottle 16 to a pressure more suitable for use by the open surgery insufflation system 10, such as about 400 kPa (about 58 psi), for example. It is possible to construct a pressure regulator 20 that could further reduce the pressure of gas supplied by the gas bottle 16; however, such a regulator would be larger and/or more complicated and may not be practical for use in a surgical setting.

In some configurations, the gas source 14 comprises a flow regulator or flow meter 22 for regulating the flow rate of the flow of insufflation gas from the gas bottle 16 or other gas supply. The flow meter 22 can be any suitable type, such as a flow meter commonly used to regulate the flow rate of medical gases (e.g., respiratory gases). The flow meter 22 can be adjustable to permit adjustment of the gas flow rate. The flow meter 22 can permit adjustment of the flow rate within any suitable range. In some configurations, the flow meter 22 can permit adjustment of the flow rate up to about 25 liters/minute (L/min). In some configurations, the flow meter 22 can permit adjustment of the flow rate to between about 1-2 L/min and about 25 L/min. More particularly, the flow meter 22 can permit adjustment of the flow rate between about 5 L/min to about 15 L/min. Even more particularly, the flow meter 22 can provide a flow rate of about 10 L/min. In some configurations, a relatively low flow rate is desired and, in some such configurations, the insufflation gas can be shielded from evacuation from the surgical site, such as with a barrier, and/or the insufflation gas level can be measured at the surgical site. If the insufflation gas level is measured, feedback control of the flow rate can be utilized. However, other suitable flow rates can also be used, which may greater than 25 L/min.

In the illustrated configuration, the gas bottle 16 (or other gas supply), pressure regulator 20 and flow meter 22 are separate from one another and coupled by suitable conduits 24. However, in other configurations, one or more of these components could be combined in an integrated unit. Other suitable arrangements are also possible.

The open surgery insufflation system 10 can also include a humidifier 30, which receives a flow of insufflation gas from the gas source 14 and outputs a warmed and humidified flow of insufflation gas. The humidifier 30 can be of any suitable arrangement, such as the humidifier 30 described below with reference to FIG. 2 or any other suitable arrangement.

The open surgery insufflation system 10 can also comprise an outlet 32 for dispensing the flow of insufflation gas. The outlet 32 can be of any suitable arrangement to deliver the flow of insufflation gas to the open surgical cavity of the patient 12. In some configurations, the outlet 32 is configured to disperse the flow of insufflation gas as it exits the outlet 32. In particular, the outlet 32 can comprise a gas diffuser of any suitable arrangement. The outlet 32 (e.g., diffuser, nozzle or other arrangement) can be referred to generally as an interface or patient interface.

The open surgery insufflation system 10 also comprises a pressure relief arrangement, which can comprise a pressure relief valve or check valve 40 (referred to hereinafter as a "pressure relief valve"). The pressure relief valve 40 can be configured to relieve pressure within the open surgery insufflation system 10 in response to system pressure above a threshold pressure level. The pressure relief valve 40 can be of any suitable type for use in a medical fluid system, such as a ball-and-spring valve, a diaphragm valve, a leaflet valve, etc. In some configurations, the threshold pressure level can be set to be slightly or significantly higher than system pressures that are expected to occur during normal use of the open surgery insufflation system 10, which can include system pressures that occur as a result of foreseeable, but less-than-ideal use of the system 10. In response to systems pressures above a threshold, the pressure relief valve 40 can open to vent pressure from the open surgery insufflation system 10, such as to the atmosphere, and reduce the system pressure. Such an arrangement can reduce the incident of or prevent failure of a system component, such as connections (e.g., taper, luer or barb connections) between components of the system 10 or, in some cases, larger system components (e.g., the humidifier 30).

Figure 2:
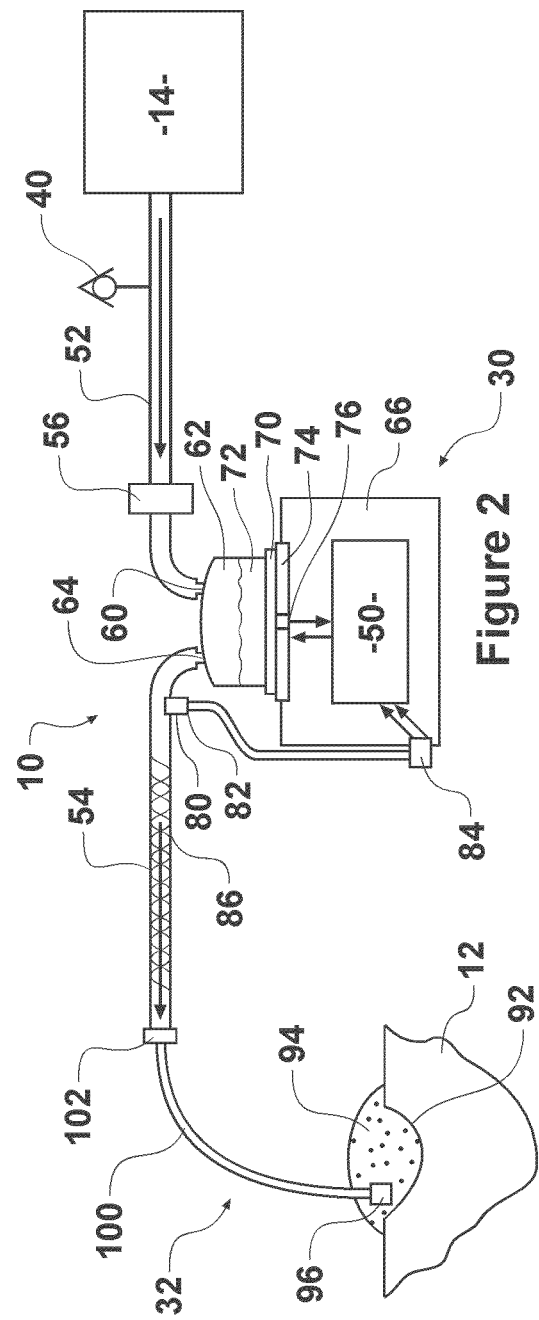
FIG. 2 illustrates the system of FIG. 1 with the humidifier and gas diffuser of the system shown in greater detail.

FIG. 2 illustrates the open surgery insufflation system 10 with an example surgical humidification system 100 for delivering temperature- and humidity-controlled gas to a patient 102 shown in greater detail. As described above, open surgery insufflation system 10 can comprise a humidifier 30, which can incorporate a humidifier control system 50. The humidifier 30 is connected to the gas source 14 through a supply conduit 52. The humidifier 30 delivers humidified gas to the patient 12 through a patient conduit 54. The conduits 52, 54 can be made of any suitable material, such as flexible plastic tubing, for example.

The humidifier 30 receives gas from the gas source 14 through the supply conduit 52. The gas can be filtered through a filter 56 and delivered to the humidifier 30 through a humidifier inlet 60. The filter 56 can be positioned at any suitable location within the system 10, such as upstream from the humidifier 30, as shown, or downstream from the humidifier 30. The gas is humidified as it passes through a humidifying chamber 62, which is effectively a water bath, and the gas flows out through a humidifier outlet 64 and into the patient conduit 54. The gas then moves through the patient conduit 54 to the patient 12. In some configurations, a filter can be disposed between the humidifier outlet 64 and the patient 12.

The humidifier 30 comprises a body or base 66 with which the humidification chamber 62 can be removably engaged. In some configurations, the humidification chamber 62 has a metal base 70 and is adapted to hold a volume of water 72, which can be heated by a heater plate 74. The heater plate 74 can be in thermal contact with the metal base 70 of the humidification chamber 62. Providing power to the heater plate 74 can cause heat to flow from the heater plate 74 to the water 72 through the metal base 70. As the water 72 within the humidification chamber 62 is heated it can evaporate and the evaporated water can mix with gases flowing through the humidification chamber 62 from the filter 56 and gas source 14. Accordingly, the humidified gases leave the humidification chamber 62 via outlet 64 and are passed to the patient 12 via the patient conduit 54 preferably to the surgical site to insufflate the surgical site.

In some configurations, the humidifier 30 includes the humidifier control system 50 configured to control a temperature and/or humidity of the gas being delivered to the patient 12. The humidifier control system 50 can be configured to regulate an amount of humidity supplied to the gases by controlling an electrical power supplied to the heater base 74. The humidifier control system 50 can control operation of the humidifier 30 in accordance with instructions set in software and in response to system inputs. System inputs can include a heater plate sensor 76, an outlet chamber temperature sensor 80, and a chamber outlet flow probe 82. For example, the humidifier control system 50 can receive temperature information from the heater plate sensor 76 which it can use as an input to a control module used to control the power or temperature set point of the heater plate 74. The humidifier control system 50 can be provided with inputs of temperature and/or flow rates of the gases. For example, the chamber outlet temperature sensor 80 can be provided to indicate to the humidifier control system 50 the temperature of the humidified gas as it leaves the outlet 64 of the humidification chamber 62. The temperature of the gases exiting the chamber can be measured using any suitable temperature sensor 80, such as a wire-based temperature sensor. The chamber outlet flow probe 82 can be provided to indicate to the humidifier control system 50 the flow rate of the humidified gas. The flow rate of the gases through the chamber 62 can be measured using any suitable flow probe 82, such as a hot wire anemometer. In some embodiments, the temperature sensor 80 and flow probe 82 are in the same sensor housing. The temperature sensor 80 and flow probe 82 can be connected to the humidifier 30 via connector 84. Additional sensors may be incorporated into the open surgery insufflation system 10, for example, for sensing parameters at the patient end of the patient conduit 54.

The humidifier control system 50 can be in communication with the heater plate 74 such that the humidifier control system 50 can control a power delivered to the heater plate 74 and/or control a temperature set point of the heater plate 74. The humidifier control system 50 can determine an amount of power to deliver to the heater plate 74, or a heater plate set point, based at least in part on a flow condition, an operation mode, a flow reading, an outlet temperature reading, a heater plate sensor reading, or any combination of these or other factors.

The open surgery insufflation system 10 can include a conduit heating wire 86 configured to provide heat to the gases traveling along the patient conduit 54. Gases leaving the outlet 64 of the humidification chamber 62 can have a high relative humidity (e.g., about 100%). As the gases travel along the patient conduit 54 there is a chance that water vapor may condense on the conduit wall, reducing the water content of the gases. To reduce condensation of the gases within the conduit 54, the conduit heating wire 86 can be provided within, throughout, and/or around the patient conduit 54. Power can be supplied to the conduit heating wire 86 from the humidifier 30 and can be controlled through the humidifier control system 50. In some configurations, the heating wire 86 is configured to maintain the temperature of the gas flowing through the patient conduit 54. In some configurations, the conduit heating wire 86 can provide additional heating of the gas to elevate the gases temperature to maintain the humidity generated by the heated water bath in the humidifier 30.

FIG. 2 also illustrates an example of an outlet 32, which can be in the form of a surgical site insufflation gas interface 32 for delivering the preferably warmed and humidified flow of insufflation gas from the patient conduit 54 to the surgical site (e.g., surgical cavity 92). The gas interface 32 can be of any suitable arrangement for delivering a flow of insufflation gas at a sufficient flow rate to create at least a partial protective environment or insufflation gas environment 94 near, at or within the surgical cavity 92. In some configurations, the gas interface 32 (in combination with a suitable gas source 14 and optional humidifier 30) can deliver a sufficient amount of insufflation gas to maintain an insufflation gas concentration (e.g., $CO_2$ concentration) of at least about 80%, or at least about 90%, within a substantial portion or an entirety of the surgical cavity 92. In some configurations, the gas interface 32 can deliver a sufficient amount of insufflation gas to maintain an insufflation gas concentration of between about 80% and about 99%, or between about 90% and about 99%, within a substantial portion or an entirety of the surgical cavity 92. In some configurations, the gas interface 32 (in combination with a suitable gas source 14 and optional humidifier 30) can deliver up to about 25 L/min. In some configurations, the gas interface 32 can deliver between about 1-2 L/min and about 25 L/min. In some configurations, the gas interface 32 can deliver between about 5 L/min and about 15 L/min, or between about 8 L/min to about 12 L/min. In some configurations, the gas interface 32 can deliver about 10 L/min.

Preferably, the gas interface 32 can deliver the insufflation gas in a manner that minimizes or eliminates any deleterious effects on the surrounding tissue. That is, preferably the gas interface 32 does not provide a jet of insufflation gas, but disperses the insufflation gas over a larger area or through multiple outlets or ports and, in at least some cases, avoids creating turbulence. In some configurations, the gas interface comprises a gas diffuser 96 for dispersing the insufflation gas from the system 10 in a diffused manner. The gas diffuser 96 can be of any suitable arrangement. In some configurations, the gas diffuser 96 is coupled to the patient conduit 54 by a conduit or tube 100. The tube 100 preferably is secured to the patient conduit 54 by a suitable connector 102, such as a luer lock connector.

In some configurations, the gas diffuser 96 comprises a porous body, which includes a large number of ports, flow paths or cavities that permit the insufflation gas to pass from the tube 100 to the atmosphere outside of the gas diffuser 96. The flow paths or cavities can be inherent in the material(s) used to construct the gas diffuser 96 or can be created within a base material(s). In some configurations, the gas diffuser 96 is constructed from a porous material, such as foam or foam-like material or sponge or sponge-like material. In some configurations, the gas diffuser 96 can be constructed from a hydrophobic material. Suitable gas diffusers 96 are marketed by Cardia Innovation AB of Stockholm, Sweden (the Vita diffuser) and Temed of Bosham, England. Examples of gas diffuser are disclosed in U.S. Pat. Nos. 6,494,858 and 6,994,685, the entireties of which are incorporated by reference herein. Other suitable gas diffusers 96 could also be used, such as perforated tubes or catheters or other perforated dispensers, for example and without limitation.

In some configurations, the tube 100 can include features to inhibit or prevent accidental occlusion, such as internal support ribs, for example. In some configurations, the tube 100 can be deformable and can be configured to hold its shape once deformed. For example, one or more of the internal ribs, a wall of the tube 100 or another portion of the tube could incorporated a malleable material that would hold the tube 100 in a desired shape once deformed. Thus, the tube 100 could be bent to allow the gas diffuser 96 to be positioned within the surgical cavity 92 and a portion of the tube 100 to be placed in contact with the patient 12 at a location adjacent to the surgical cavity 92. If desired, the tube 100 can be secured in place.

As described above, the open surgery insufflation system 10 preferably includes a pressure relief arrangement, which can be a pressure relief valve 40. The pressure relief valve 40 can relieve or vent pressure from within the system 10 if the system pressure reaches or exceeds a threshold pressure. The system 10 could reach or exceed the threshold pressure as a result of the partial or complete occlusion of a passage within the system 10, such as within the supply conduit 52, patient conduit 54, tube 100 or gas diffuser 96, for example and without limitation. The pressure relief valve 40 can be positioned at any suitable location within the system 10. In some configurations, the pressure relief valve 40 is located in a non-sterile portion of the open surgery insufflation system 10 when the system 10 is in normal use under normal circumstances. For example, a portion of the system 10 from the gas source 14 up to and including the humidifier 30 can be non-sterile in normal use. A sterile portion of the system 10 can include the gas diffuser 96, tube 100 and connector 102, which can be an integrated assembly in some cases. The patient conduit 54 can be sterile, non-sterile or can have portions that are within the sterile field and portions that are within the non-sterile field.

Positioning the pressure relief valve 40 in the non-sterile field or within a non-sterile area is advantageous because the pressure relief valve 40 can be re-used. In some configurations, as illustrated in FIG. 2, the pressure relief valve 40 can be positioned upstream of the humidifier 30 relative to a direction of the gas flow. In some configurations, the pressure relief valve 40 can be positioned between the gas source 14 and the humidifier 30. In particular, the pressure relief valve 40 can be positioned between the flow meter 22 and the humidifier 30. In some configurations, the pressure relief valve 40 can be positioned along or integrated into the supply conduit 52. For example, the pressure relief valve 40 can be coupled to a pair of conduit portions of the supply conduit 52 by a tee connection, such as an NPT threaded ¼ inch tee connection, for example and without limitation.

In other configurations, the pressure relief valve 40 can be positioned downstream of the humidifier 30 and/or within a sterile portion of the open surgery insufflation system 10. One such optional arrangement is illustrated in FIG. 3. In such arrangements, the pressure relief valve 40 can be a consumable or disposable component of the system 10. In some configurations, the pressure relief valve 40 can be positioned between the humidifier 30 and the diffuser 32. In some such configurations, the pressure relief valve 40 can be positioned along, or integrated into, the patient conduit 54 (e.g., as described above with respect to the supply conduit 52), between the patient conduit 54 and the diffuser 32, or integrated within the diffuser 32.

In use, the components of the system 10 can be assembled, if necessary. Supply of insufflation gas from the gas source 14 can be initiated, such as by opening the valve of the gas bottle 16 or other gas supply, for example. If necessary, the flow meter 22 can be adjusted to achieve a desirable flow rate of the insufflation gas. If present, the humidifier 30 can be turned on and adjusted to warm and humidify the insufflation gas to a desirable level. The gas diffuser 96 of the gas interface 32 can be positioned within the surgical cavity 92 of the patient 12 to create an insufflation gas environment 94, which can be maintained throughout completion of the surgical procedure. In the event of a rise in system pressure above a threshold pressure, the pressure relief valve 40 can activate, open or vent the flow of insufflation gas to reduce the system pressure.

It has been unexpectedly discovered by the present inventor that, although the open surgery insufflation system 10 is an open system that dispenses insufflation gas to a generally open atmosphere that normally results in a low system pressure, occlusions can occur within the system 10 during normal, or at least foreseeable, use that can cause a significant rise in the system pressure. In some cases, the rise in system pressure can be sufficient, in the absence of a pressure relief arrangement 40, to cause temporary or permanent damage to components of the system 10. For example, elevated system pressure can cause the disconnection of components of the system 10, such as the supply conduit 52 with the flow meter 22, for example, which may be a hose and barb connection. In some cases, the disconnection can be of a luer lock connection, taper connection or other type of connection. In some cases, elevated system pressure can cause permanent damage, such as damage to the humidifier 30 (e.g., the humidifying chamber 62), for example. Damage to the system 10, temporary or permanent, can cause an interruption or cessation of the insufflation therapy, which is undesirable at the least.

It has been discovered that some causes for occlusion of the system 10 include, for example and without limitation, manipulation of the gas diffuser 96 (e.g., depression of the diffuser material during placement or to evacuate fluid build-up in the diffuser material), manipulation (e.g., bending) of the tube 100, submersion of the gas diffuser 96 in fluid, and the gas diffuser 96 being adjacent to or surrounded by an object that partially or completely blocks flow, such as a semi-solid or a solid material (e.g., gauze, organs), for example and without limitation. In some cases, these actions or activities result in modest increases of the system pressure that do not pose a significant risk of damage or interruption of the insufflation therapy. However, in some cases, such actions or activities could result in significant increases in system pressure that could create a significant risk of damage or interruption of the insufflation therapy.

The present inventor has investigated the system pressure increases caused by these and similar actions or activities, as well as the system pressures that could cause damage to the system 10. For example, the connection strength of the various connections between components and conduits of the system 10 was evaluated. As a result, it was determined that a preferred pressure relief valve 40 should open or vent system pressure at a threshold pressure of no more than about 83 kPa (12 pounds per square inch (psi)). In some configurations, it is preferable for the threshold pressure for opening or venting of the pressure relief valve 40 to be no more than about 65.5 kPa (9.5 psi). In some configurations, it is desirable for the threshold pressure for opening or venting of the pressure relief valve 40 to be no more than about 34.5 kPa (5 psi). Such opening or venting threshold have been determined to be suitable to reduce or eliminate the risk of damage to the system 10 or interruption of the insufflation therapy.

In some configurations, it is desirable to avoid opening or venting the pressure relief valve 40 in response to elevations in system pressure that are not likely to be harmful to components of the system 10. Thus, in some configurations, it is desirable to configure the pressure relief valve 40 to remain closed or not vent in response to system pressure lower than about 14 kPa (2 psi). In some configurations, it is desirable to configure the pressure relief valve 40 to remain closed or not vent in response to system pressure lower than about 24 kPa (3.5 psi). Thus, in some configurations, it is desirable to configure the pressure relief valve 40 to have an opening or venting threshold pressure of between about 14 kPa (2 psi) to about 83 kPa (12 psi), or between about 14 kPa (2 psi) to about 34.5 kPa (5 psi). In other configurations, it is desirable to configure the pressure relief valve 40 to have an opening or venting threshold pressure of between about 21 kPa (3 psi) to about 83 kPa (12 psi), or between about 21 kPa (3 psi) to about 65.5 kPa (9.5 psi). Any values or ranges within the above-recited ranges are also contemplated. In other configurations, or other applications, the pressure relief valve 40 may be configured to have a higher activation, opening or venting pressure threshold. In some configurations, the pressure threshold of the pressure relief valve 40 is fixed and/or preset. In other configurations, the pressure threshold could be adjustable, such as adjustable within one or more of the ranges identified herein.

Figure 4A:
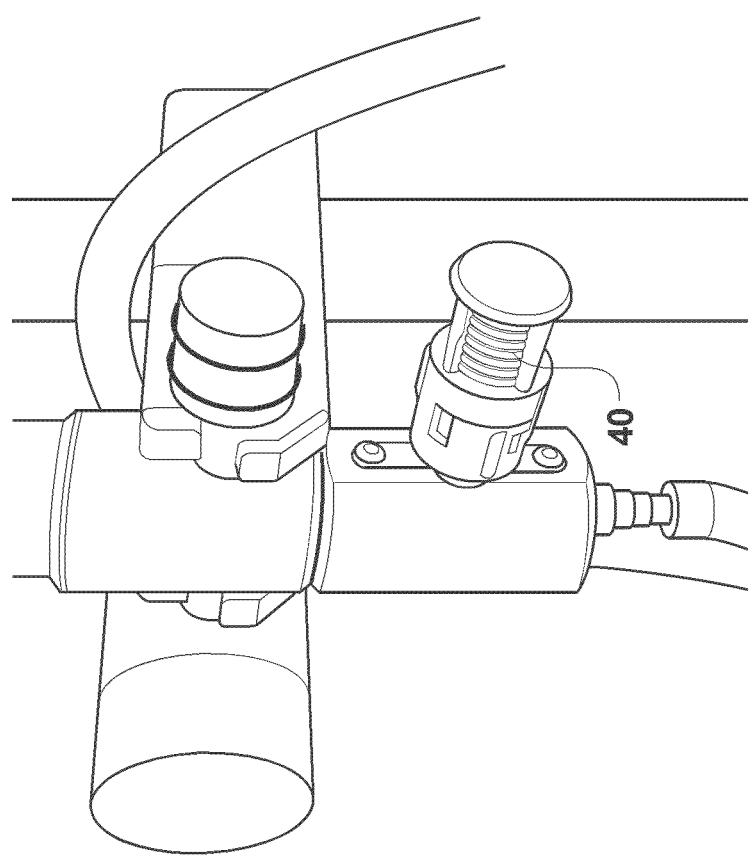

With additional reference to FIGS. 4a and 4b, the pressure relief valve 40 may be provided with a protective shroud 110 which at least partially encloses the pressure relief valve 40 so that the valve 40 is protected from detritus, such as dust, settling on it. Without the shroud 110, the valve 40, when it triggers, might blast any dust from the valve 40 into the room, which is not desirable in a surgical environment. The shroud 110 also helps to prevent any unintentional disconnection of the pressure relief valve 40.

FIG. 4a shows an example pressure relief valve 40, without the shroud 110 attached. In FIG. 4b, the pressure relief valve 40 has been substantially encased in the shroud 110. The shroud 110 in this example substantially covers the length of the pressure relief valve 40, but has a gap 112 at one end to allow the gas to escape when the pressure relief valve 40 triggers. In this example, the shroud 110 comprises an open ended cylindrical cover inside which the valve 40 is received. The shroud 11 may be permanently mounted, or removable.

Unless the context clearly requires otherwise, throughout the description and the claims, the words "comprise", "comprising", and the like, are to be construed in an inclusive sense as opposed to an exclusive or exhaustive sense, that is to say, in the sense of "including, but not limited to".

Reference to any prior art in this specification is not, and should not be taken as, an acknowledgement or any form of suggestion that that prior art forms part of the common general knowledge in the field of endeavour in any country in the world.

The invention may also be said broadly to consist in the parts, elements and features referred to or indicated in the specification of the application, individually or collectively, in any or all combinations of two or more of said parts, elements or features.

Where, in the foregoing description reference has been made to integers or components having known equivalents thereof, those integers are herein incorporated as if individually set forth.

It should be noted that various changes and modifications to the presently preferred embodiments described herein will be apparent to those skilled in the art. Such changes and modifications may be made without departing from the spirit and scope of the invention and without diminishing its attendant advantages. For instance, various components may be repositioned as desired. It is therefore intended that such changes and modifications be included within the scope of the invention. Moreover, not all of the features, aspects and advantages are necessarily required to practice the present invention. Accordingly, the scope of the present invention is intended to be defined only by the claims that follow.

What is claimed is:

1. An open surgical insufflation system, comprising:
  a gas source for providing a flow of insufflation gas, wherein the gas source comprises a gas bottle, a pressure regulator, and a flow meter;
  a humidifier that receives the flow of insufflation gas from the gas source, wherein the humidifier warms and humidifies the flow of insufflation gas;
  a gas diffuser that dispenses the warmed and humidified flow of insufflation gas from the humidifier to an open surgical cavity in direct contact with an external atmosphere to create an insufflation gas environment in the open surgical cavity; and
  a pressure relief arrangement that has an outlet to atmosphere separate from the gas diffuser, the pressure relief arrangement being activated in response to a system pressure above a threshold pressure and operating to reduce the system pressure when activated, the pressure relief arrangement being positioned in series along a gas flow path of the open surgical insufflation system and downstream of the pressure regulator of the gas source.

2. The open surgical insufflation system of claim 1, wherein the pressure relief arrangement is located between the gas source and the humidifier.

3. The open surgical insufflation system of claim 1, wherein the pressure relief arrangement is located upstream from the humidifier relative to a direction of the flow of insufflation gas within the system, and wherein the humidifier is positioned in series with the pressure relief arrangement along the gas flow path.

4. The open surgical insufflation system of claim 1, wherein the pressure relief arrangement is located downstream from the humidifier relative to a direction of the flow of insufflation gas within the system.

5. The open surgical insufflation system of claim 1, wherein the threshold pressure is no greater than about 12 psi.

6. The open surgical insufflation system of claim 1, wherein the threshold pressure is no greater than about 9.5 psi.

7. The open surgical insufflation system of claim 1, wherein the threshold pressure is no greater than about 5 psi.

8. The open surgical insufflation system of claim 1, wherein the threshold pressure is between about 2 psi and about 9.5 psi.

9. The open surgical insufflation system of claim 1, wherein the threshold pressure is between about 3 psi and about 5 psi.

10. The open surgical insufflation system of claim 1, wherein the flow meter is adjustable and permits a flow rate of the flow of insufflation gas to be adjusted to between about 1 L/min and about 25 L/min.

11. The open surgical insufflation system of claim 1, wherein the flow meter is adjustable and permits a flow rate of the flow of insufflation gas to be adjusted to between about 5 L/min and about 15 L/min.

12. The open surgical insufflation system of claim 11, wherein the flow rate can be adjusted to about 10 L/min.

13. The open surgical insufflation system of claim 1, wherein the gas diffuser is constructed from a foam or foam-like material.

14. A method of providing insufflation gas therapy in an open surgical procedure, comprising:
providing a flow of an insufflation gas from a gas source, the gas source comprising a pressure regulator;
passing the flow of insufflation gas through a humidifier to warm and humidify the flow of insufflation gas;
dispensing the gas through a gas diffuser to a surgical cavity that is open to the atmosphere to create an insufflation gas environment in the surgical cavity; and
relieving pressure within a system comprising the gas source, the humidifier, and the gas diffuser through a pressure relief arrangement that has an outlet to atmosphere separate from the gas diffuser in response to an increase in pressure within the system above a threshold pressure, wherein the pressure relief arrangement is positioned downstream of the pressure regulator of the gas source.

15. The method of claim 14, wherein the pressure relief arrangement is located between the gas source and the humidifier.

16. The method of claim 14, wherein the pressure relief arrangement is located upstream from the humidifier relative to a direction of the flow of insufflation gas within the system, and wherein the humidifier is positioned in series with the pressure relief arrangement.

17. The method of claim 14, wherein the pressure relief arrangement is located downstream from the humidifier relative to a direction of the flow of insufflation gas within the system.

18. The method of claim 14, wherein the threshold pressure is no greater than about 12 psi.

19. The method of claim 14, wherein the threshold pressure is no greater than about 9.5 psi.

20. The method of claim 14, wherein the threshold pressure is no greater than about 5 psi.

21. The method of claim 14, wherein the threshold pressure is between about 2 psi and about 9.5 psi.

22. The method of claim 14, wherein the threshold pressure is between about 3 psi and about 5 psi.

23. The method of claim 14, wherein the gas source further comprises a gas bottle and a flow meter.

24. The method of claim 23, further comprising adjusting the flow meter so that a flow rate of the flow of insufflation gas is between about 5 L/min and about 15 L/min.

25. The method of claim 23, further comprising adjusting the flow meter so that a flow rate of the flow of insufflation gas is between about 5 L/min and about 15 L/min.

26. The method of claim 25, further comprising adjusting the flow rate to about 10 L/min.

27. The method of claim 14, wherein the gas diffuser is constructed from a foam or foam-like material.

28. A method of assembling an open surgical insufflation system, comprising:
connecting a gas source to a humidifier, the gas source configured to supply a flow of insufflation gas to the humidifier and the humidifier configured to receive the flow of insufflation gas and warm and humidify the flow of insufflation gas, wherein the gas source comprises a pressure regulator;
connecting a gas diffuser to the humidifier, the gas diffuser configured to dispense the flow of insufflation gas from the humidifier to an open surgical cavity of a patient;
connecting a pressure relief arrangement to the system, the pressure relief arrangement having an outlet to atmosphere separate from the gas diffuser and being configured to reduce pressure within the system when the pressure reaches a threshold pressure, wherein the pressure relief arrangement is positioned downstream of the pressure regulator of the gas source.

29. The method of claim 28, wherein connecting the pressure relief arrangement comprises connecting the pressure relief arrangement between the gas source and the humidifier.

30. The method of claim 28, wherein connecting the pressure relief arrangement comprises connecting the pressure relief arrangement at a location upstream from the humidifier relative to a direction of the flow of insufflation gas within the system, and wherein the humidifier is positioned in series with the pressure relief arrangement.

31. The method of claim 28, wherein connecting the pressure relief arrangement comprises connecting the pressure relief arrangement at a location downstream from the humidifier relative to a direction of the flow of insufflation gas within the system.

32. The method of claim 28, wherein the threshold pressure is no greater than about 12 psi.

33. The method of claim 28, wherein the threshold pressure is no greater than about 9.5 psi.

34. The method of claim 28, wherein the threshold pressure is no greater than about 5 psi.

35. The method of claim 28, wherein the threshold pressure is between about 2 psi and about 9.5 psi.

36. The method of claim 28, wherein the threshold pressure is between about 3 psi and about 5 psi.

37. The method of claim 28, wherein the gas source further comprises a gas bottle and a flow meter.

38. The open surgical insufflation system of claim 1, wherein the pressure relief arrangement is positioned within a non-sterile portion of the system.

* * * * *